United States Patent
Flanagan et al.

(10) Patent No.: US 12,015,899 B2
(45) Date of Patent: Jun. 18, 2024

(54) LIGHT SENSOR IN HEARING INSTRUMENT

(71) Applicant: Starkey Laboratories, Inc., Eden Prairie, MN (US)

(72) Inventors: Peter Flanagan, St. Louis Park, MN (US); Kyle Olson, St. Louis Park, MN (US); Michael Karl Sacha, Chanhassen, MN (US); Andy S. Lin, Chanhassen, MN (US); Fa Wang, Bloomington, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 164 days.

(21) Appl. No.: 17/811,759

(22) Filed: Jul. 11, 2022

(65) Prior Publication Data

US 2022/0345835 A1     Oct. 27, 2022

Related U.S. Application Data

(63) Continuation of application No. PCT/US2021/012956, filed on Jan. 11, 2021.
(Continued)

(51) Int. Cl.
*H04R 25/00* (2006.01)
*A61B 5/00* (2006.01)
(Continued)

(52) U.S. Cl.
CPC ....... *H04R 25/505* (2013.01); *A61B 5/02416* (2013.01); *A61B 5/6817* (2013.01);
(Continued)

(58) Field of Classification Search
CPC ...... A61B 5/01; A61B 5/02055; G01K 13/20; H04R 25/505; H04R 2225/41; H04R 2225/31; H04R 25/658
See application file for complete search history.

(56) References Cited

U.S. PATENT DOCUMENTS

| 7,614,866 B2 | 11/2009 | Sperry et al. |
| 7,764,380 B2 | 7/2010 | Van Hal et al. |
| (Continued) | | |

FOREIGN PATENT DOCUMENTS

| CN | 104427960 A | 3/2015 |
| CN | 105230141 A | 1/2016 |
| (Continued) | | |

OTHER PUBLICATIONS

"Fingertip size, ultra-compact spectrometer head integrating MEMS and image sensor technologies", Hamamatsu, Retrieved from: https://www.hamamatsu.com/us/en/product/optical-sensors/spectrometers/mini-spectrometer/C12666MA.html; Accessed on Nov. 8, 2019; 6 pp.
(Continued)

*Primary Examiner* — Brian Ensey
(74) *Attorney, Agent, or Firm* — Shumaker & Sieffert, P.A.

(57) ABSTRACT

A system may have a rechargeable hearing instrument with a power source, an ultraviolet (UV) sensor configured to convert received UV light into electrical power and charging circuitry coupled to the UV sensor and to the power source. The charging circuitry may use the electrical power to charge the power source. A charger may have a charging cavity configured to receive the rechargeable hearing instrument. A power source within the charger powers a UV light source located within the charger configured to provide UV light to the UV sensor of the rechargeable hearing instrument when the rechargeable hearing instrument is placed within the charging cavity.

16 Claims, 9 Drawing Sheets

Related U.S. Application Data

(60) Provisional application No. 62/961,021, filed on Jan. 14, 2020.

(51) Int. Cl.
*A61B 5/024* (2006.01)
*G01J 1/42* (2006.01)
*G01J 3/28* (2006.01)

(52) U.S. Cl.
CPC ............. *G01J 1/4204* (2013.01); *G01J 1/429* (2013.01); *G01J 3/28* (2013.01); *G01J 2001/4266* (2013.01); *H04R 2225/41* (2013.01)

(56) References Cited

U.S. PATENT DOCUMENTS

| | | | |
|---|---|---|---|
| 8,032,337 | B2 | 10/2011 | Deichmann et al. |
| 8,184,837 | B2 | 5/2012 | Poh |
| 8,478,587 | B2 | 7/2013 | Kawamura et al. |
| 9,289,175 | B2 | 3/2016 | Leboeuf et al. |
| 9,579,060 | B1 | 2/2017 | Lisy et al. |
| 10,154,332 | B2 * | 12/2018 | Hirsch ................. H04R 1/1041 |
| 10,341,787 | B2 | 7/2019 | Blum et al. |
| 10,424,955 | B2 | 9/2019 | Higgins et al. |
| 10,571,715 | B2 | 2/2020 | Rizzo, III et al. |
| 11,029,198 | B2 | 6/2021 | Rogers et al. |
| 2004/0017300 | A1 | 1/2004 | Kotzin et al. |
| 2006/0269111 | A1 | 11/2006 | Stoecker et al. |
| 2010/0020993 | A1 * | 1/2010 | Poh ...................... H04R 25/505 381/322 |
| 2011/0135126 | A1 | 6/2011 | Gozen |
| 2015/0264721 | A1 | 9/2015 | Shilton |
| 2017/0112671 | A1 | 4/2017 | Goldstein |
| 2017/0171046 | A1 | 6/2017 | Flood et al. |
| 2017/0238812 | A1 | 8/2017 | Atlas |
| 2018/0206045 | A1 | 7/2018 | Johnson et al. |
| 2018/0302709 | A1 | 10/2018 | Wagner et al. |
| 2019/0117155 | A1 | 4/2019 | Cross et al. |

FOREIGN PATENT DOCUMENTS

| | | |
|---|---|---|
| CN | 107923988 A | 4/2018 |
| ES | 2378060 T3 | 4/2012 |
| JP | WO2008126347 A1 | 7/2010 |
| WO | 2014051789 A1 | 4/2014 |

OTHER PUBLICATIONS

"How to Use My Skin Track UV Sensor | La Roche-Posay", Youtube, Retrieved from: https://www.youtube.com/watch?v=JUizcdUKeEl, Mar. 20, 2019; 1 pp.

"My UV Patch", Youtube, Retrieved from: https://www.youtube.com/watch; Apr. 18, 2016; 7 pp.

International Preliminary Report on Patentability from International Application No. PCT/US2021/012956 dated Jul. 28, 2022, 16 pp.

International Search Report and Written Opinion of International Application No. PCT/US2021/012956 dated Jun. 1, 2021, 22 pp.

* cited by examiner

LIGHT SENSOR IN HEARING INSTRUMENT

This application is a continuation of International Application No. PCT/US2021/012956, filed Jan. 11, 2021, which claims the benefit of U.S. Provisional Patent Application 62/961,021, filed Jan. 14, 2020, the entire content of both of which are incorporated by reference herein.

TECHNICAL FIELD

This disclosure relates to hearing instruments.

BACKGROUND

Hearing instruments are devices designed to be worn on, in, or near one or more of a user's ears. Common types of hearing instruments include hearing assistance devices (e.g., "hearing aids"), earbuds, headphones, hearables, cochlear implants, and so on. In some examples, a hearing instrument may be implanted or integrated into a user. Some hearing instruments include additional features beyond just environmental sound-amplification. For example, some modern hearing instruments include advanced audio processing for improved device functionality, controlling and programming the devices, and beamforming, and some may even communicate wirelessly with external devices including other hearing instruments (e.g., for streaming media).

SUMMARY

This disclosure describes techniques for determining whether a user of a hearing instrument is located either indoors or outdoors. The hearing instrument may have an ultraviolet (UV) sensor, a photoplethysmography (PPG) sensor and/or a spectrometer on board the hearing instrument to determine whether the user is located indoors or outdoors. The hearing instrument may use energy converted by the UV sensor to charge a power source used by the hearing instrument. The UV sensor may also be used in the manufacturing process of the hearing instrument by detecting UV light used in the curing of an adhesive used in the manufacturing of the hearing instrument. Processing circuitry onboard the hearing instrument may use the data from the UV sensor to determine whether the adhesive is properly cured and thus improve the manufacturing process for the hearing instrument. The UV sensor may also work with other onboard sensors, such as the PPG sensor to determine if the user has hair or a head covering which is blocking the hearing instrument. If a user's hair or head covering is detected, the processing circuitry may adjust a pre-established heat balance equation, which determines a user's temperature.

In an example according to the disclosure, a system may have a rechargeable hearing instrument with a power source, an ultraviolet (UV) sensor configured to convert received UV light into electrical power and charging circuitry coupled to the UV sensor and to the power source. The charging circuitry may use the electrical power to charge the power source. A charger may have a charging cavity configured to receive the rechargeable hearing instrument. A power source within the charger powers a UV light source located within the charger configured to provide UV light to the UV sensor of the rechargeable hearing instrument when the rechargeable hearing instrument is placed within the charging cavity.

In another example this disclosure describes a method for operating a hearing instrument, the method comprising the following steps: measuring an ambient light level at the hearing instrument to provide a measurement result; recording the measurement result; determining a delta ambient light level based on the detected ambient light level; recording the delta ambient light level; determining whether an absolute value of the delta ambient light level exceeds a predetermined threshold; determining, based on the absolute value of the delta ambient light level exceeding the predetermined threshold and the delta ambient light level being positive, a user has moved to an outdoor environment; and setting a signal processing parameter of the hearing instrument as a function of the determination the user is in the outdoor environment or an indoor environment.

In another example this disclosure describes a method implemented by a hearing instrument configured for insertion into an ear canal of an ear of a user of the hearing instrument, the method comprising: measuring, with a first temperature sensor, a first temperature of the ear canal; measuring, with a second temperature sensor, a second temperature at a location spaced apart from a surface of the ear canal; detecting, using processing circuitry of the hearing instrument and data received from an ultraviolet (UV) sensor, whether the ear canal is at least partially covered; storing, in a memory of the hearing instrument, a pre-established heat balance equation that the processing circuitry utilizes to compensate the heat balance equation based on the ear canal being at least partially covered; and calculating, using the processing circuitry of the hearing instrument, a body temperature of the user using the heat balance equation and the first and second temperatures.

In another example, this disclosure describes a method of manufacturing a hearing instrument, the method comprising: preparing a hearing instrument housing for ultraviolet (UV) adhesive application; applying a UV adhesive to the hearing instrument housing; detecting, with a UV sensor coupled to the hearing instrument, a predetermined amount of UV light; determining, by processing circuitry, when the predetermined amount of UV light is detected; and communicating, by the processing circuitry, completion of the UV light detection process.

In another example, this disclosure describes a method for operating a hearing instrument, the method comprising the following steps: detecting an ultraviolet (UV) light level at the hearing instrument; detecting an infrared light level; determining, based on the UV light level and the infrared light level are consistent with the user being outdoors, that the hearing instrument is uncovered; and determining, based on the UV light level not being consistent with the user being outdoors, that the hearing instrument is covered.

In another example, this disclosure describes a system comprising a rechargeable hearing instrument that comprises: a hearing instrument power source; an ultraviolet (UV) sensor configured to convert received UV light into electrical power; and charging circuitry operatively coupled to the UV sensor and to the power source, wherein the charging circuitry uses the electrical power to charge the power source.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

It may be advantageous to determine the type of environment a hearing instrument user is in. As described in this disclosure, one or more processors of the hearing instrument may determine the type of environment based, at least in part, by monitoring lighting conditions via onboard sensors in the hearing instrument. However, it may be difficult to quantify the light-based environment the user is in. To provide better services for a hearing instrument user, it may be desirable to know what the user is doing in their daily lives. It may also be desirable to know when a user may be in harmful environments, such as sun overexposure. Using light sensors built into a hearing instrument (e.g., a hear rate sensor) to track the amount of light exposure a user may be subject to as an input for activity monitoring applications, social engagement applications, energy expenditure applications and outdoors applications. It may also be desirable to track the amount of UV light exposure. Tracking time spent outdoors and to notify the user when they have reached thresholds of UV exposure. A UV sensor may allow for detection of UV light.

Figure 1:
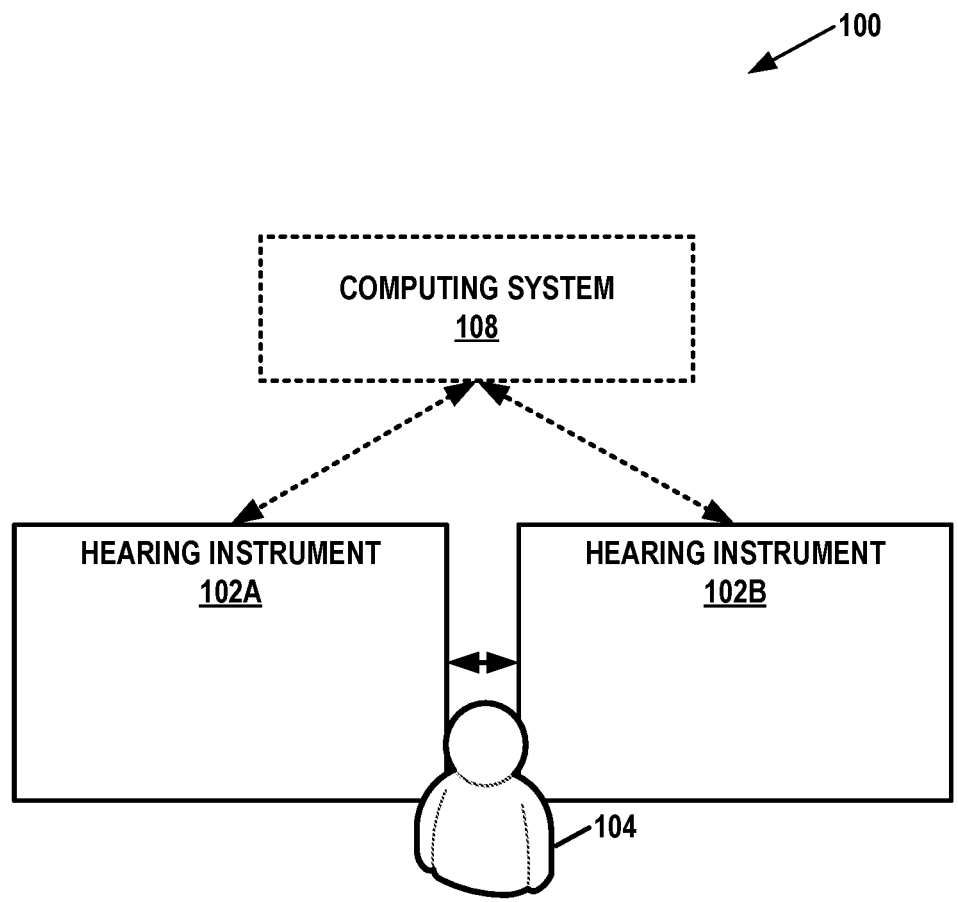
FIG. 1 is a conceptual diagram illustrating an example system including one or more hearing instruments, in accordance with one or more techniques of this disclosure.

FIG. 1 is a conceptual diagram illustrating an example system 100 including hearing instruments 102A, 102B, in accordance with one or more techniques of this disclosure. This disclosure may refer to hearing instruments 102A and 102B collectively, as "hearing instruments 102." A user 104 may wear hearing instruments 102. In some instances, such as when user 104 has unilateral hearing loss, user 104 may wear a single hearing instrument. In other instances, such as when user 104 has bilateral hearing loss, the user may wear two hearing instruments, with one hearing instrument for each ear of the user. For purposes of discussion any reference to hearing instrument 102A may apply equally to hearing instrument 102B.

Hearing instruments 102 may comprise one or more of various types of devices configured to provide auditory stimuli to a user and designed for wear and/or implantation at, on, or near an ear of the user. Hearing instruments 102 may be worn, at least partially, in the ear canal or concha. One or more of hearing instruments 102 may include behind the ear (BTE) components worn behind the ears of user 104. In some examples, hearing instruments 102 comprise devices at least partially implanted into or osseointegrated with the skull of the user. In some examples, one or more of hearing instruments 102 are able to provide auditory stimuli to user 104 via a bone conduction pathway.

In any of the examples of this disclosure, each of hearing instruments 102 may comprise a hearing assistance device. Hearing assistance devices 102 include devices helping a user hear sounds in the user's environment. Example types of hearing assistance devices may include hearing aid devices, Personal Sound Amplification Products (PSAPs), cochlear implant systems (which may include cochlear implant magnets, cochlear implant transducers, and cochlear implant processors), and so on. In some examples, hearing instruments 102 are over-the-counter, direct-to-consumer, or prescription devices. Furthermore, in some examples, hearing instruments 102 include devices providing auditory stimuli to the user corresponding to artificial sounds or sounds not naturally in the user's environment, such as recorded music, computer-generated sounds, or other types of sounds. For instance, hearing instruments 102 may include so-called "hearables", earbuds, earphones, or other types of devices. Some types of hearing instruments provide auditory stimuli to the user corresponding to sounds from the user's environmental and also artificial sounds.

In some examples, one or more of hearing instruments 102 includes a housing or shell designed to be worn in the ear for both aesthetic and functional reasons and encloses the electronic components of the hearing instrument. Such hearing instruments may be referred to as in-the-ear (ITE), in-the-canal (ITC), completely-in-the-canal (CIC), or invisible-in-the-canal (IIC) devices. In some examples, one or more of hearing instruments 102 may be behind-the-ear (BTE) devices, which include a housing worn behind the ear containing all of the electronic components of the hearing instrument, including the receiver (e.g., a speaker). The receiver conducts sound to an earbud inside the ear via an audio tube. In some examples, one or more of hearing instruments 102 may be receiver-in-canal (RIC) hearing-assistance devices, which include a housing worn behind the ear containing electronic components and a housing worn in the ear canal containing the receiver.

Hearing instruments 102 may implement a variety of features helping user 104 hear better. For example, hearing instruments 102 may amplify the intensity of incoming sound, amplify the intensity of certain frequencies of the incoming sound, translate or compress frequencies of the incoming sound, and/or perform other functions to improve the hearing of user 104. In another example, hearing instruments 102 may implement a directional processing mode in which hearing instruments 102 selectively amplify sound originating from a particular direction (e.g., to the front of the user) while potentially fully or partially canceling sound originating from other directions. In other words, a directional processing mode may selectively attenuate off-axis unwanted sounds. The directional processing mode may help users understand conversations occurring in crowds or other noisy environments. In some examples, hearing instruments 102 may use beamforming or directional processing cues to implement or augment directional processing modes.

In some examples, hearing instruments 102 may reduce noise by canceling out or attenuating certain frequencies. Furthermore, in some examples, hearing instruments 102 may help user 104 enjoy audio media, such as music or sound components of visual media, by outputting sound based on audio data wirelessly transmitted to hearing instruments 102.

Hearing instruments 102 may be configured to communicate with each other. For instance, in any of the examples of this disclosure, hearing instruments 102 may communicate with each other using one or more wireless communication technologies. Example types of wireless communication technology include Near-Field Magnetic Induction (NFMI) technology, a 900 MHz technology, a BLUETOOTH™ technology, a WI-FI™ technology, audible sound signals, ultrasonic communication technology, infrared communication technology, an inductive communication technology, or another type of communication not relying on wires to transmit signals between devices. In some examples, hearing instruments 102 use a 2.4 GHz frequency band for wireless communication. In examples of this disclosure, hearing instruments 102 may communicate with each other via non-wireless communication links, such as via one or more cables, direct electrical contacts, and so on.

As shown in the example of FIG. 1, system 100 may also include a computing system 108. In other examples, system 100 does not include computing system 108. Computing system 108 comprises one or more computing devices, each of which may include one or more processors. For instance, computing system 108 may comprise one or more mobile devices, server devices, personal computer devices, handheld devices, wireless access points, smart speaker devices, smart televisions, medical alarm devices, smart key fobs, smartwatches, smartphones, motion or presence sensor devices, smart displays, screen-enhanced smart speakers, wireless routers, wireless communication hubs, prosthetic devices, mobility devices, special-purpose devices, accessory devices, and/or other types of devices. Accessory devices may include devices configured specifically for use with hearing instruments 102. Example types of accessory devices may include charging cases for hearing instruments 102, storage cases for hearing instruments 102, media streamer devices, phone streamer devices, external microphone devices, remote controls for hearing instruments 102, and other types of devices specifically designed for use with hearing instruments 102. Actions described in this disclosure as being performed by computing system 108 may be performed by one or more of the computing devices of computing system 108. One or more of hearing instruments 102 may communicate with computing system 108 using wireless or non-wireless communication links. For instance, hearing instruments 102 may communicate with computing system 108 using any of the example types of communication technologies described elsewhere in this disclosure.

In an example of FIG. 1, hearing instruments 102 may determine whether user 104 is in an indoor environment or an outdoor environment. Onboard sensors are configured to detect environmental conditions which assist hearing instruments 102 in determining a user's environment: indoors or outdoors. In another example, hearing instruments 102 are able to determine whether a user's hair, ear muffs, hat coat, etc. is obfuscating or covering hearing instruments 102. If hearing instruments 102 detect the user's hair is covering hearing instruments 102, a correction may be applied to properly determine the user's body temperature as hair covering the hearing instrument may provide a false temperature reading of the user. In another example, hearing instruments 102 are configured to be charged with UV wavelengths. Hearing instruments 102 may have a UV sensor which senses and converts UV wavelengths into electrical energy which may be used to charge an onboard power source. In another example, a hearing instrument charger may have a UV source which may be used to couple with the hearing instrument UV sensor to charge the onboard power source. In another example, the UV sensor may be used during the hearing instrument manufacturing process. The UV sensor may be utilized during UV curing of UV-curable materials, such as coatings and adhesives. The UV sensor may detect when the UV-curable materials are cured to a particular level based on the amount of UV light which is transferred to the UV sensor.

Figure 2:
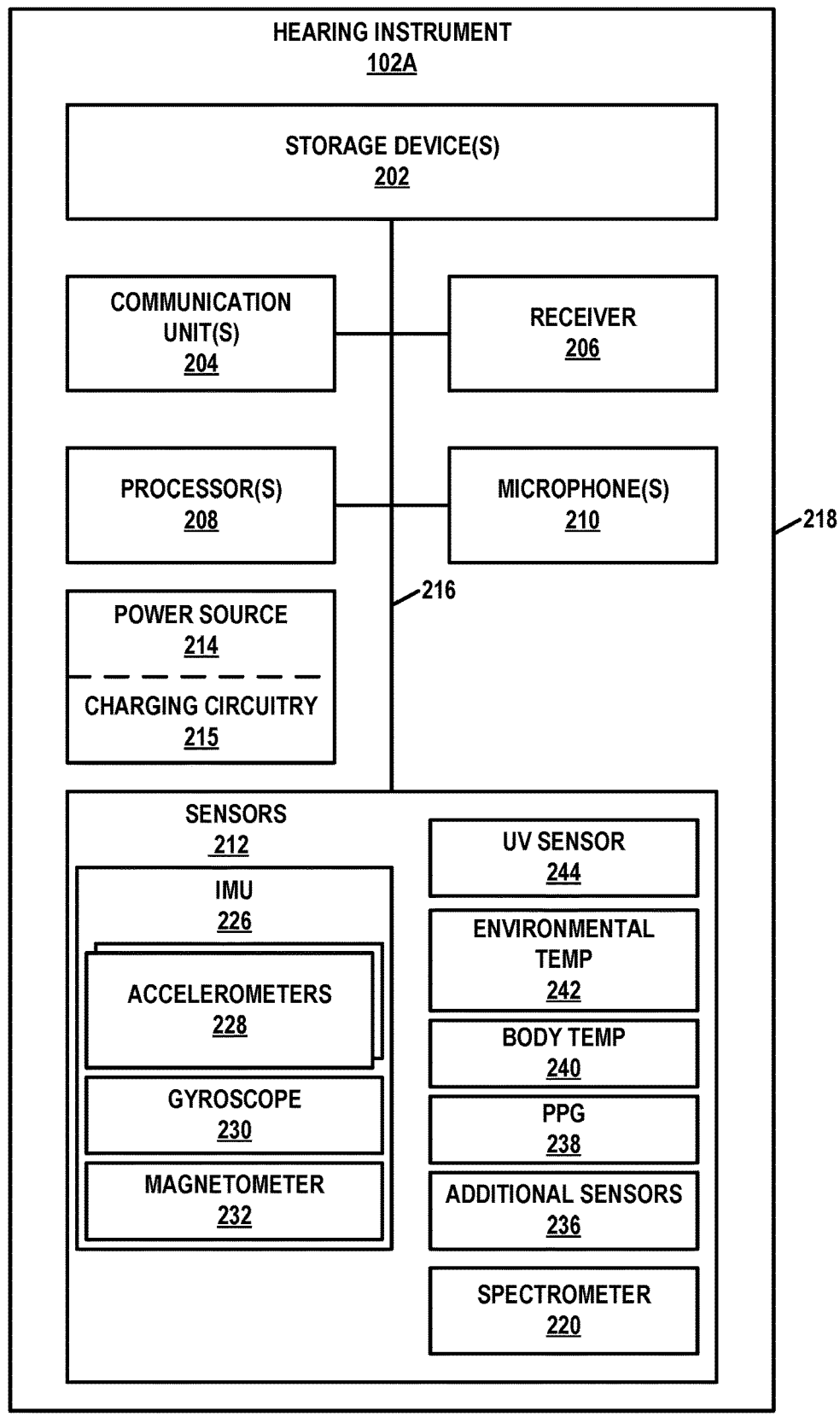
FIG. 2 is a block diagram illustrating example components of a hearing instrument, in accordance with one or more techniques of this disclosure.

FIG. 2 is a block diagram illustrating example components of hearing instrument 102A, in accordance with one or more techniques of this disclosure. Hearing instrument 102B may include the same or similar components of hearing instrument 102A shown in the example of FIG. 2. In the example of FIG. 2, hearing instrument 102A comprises one or more storage devices 202, one or more communication units 204, a receiver 206, one or more processors 208, one or more microphones 210, a set of sensors 212, a power source 214, one or more communication channels 216 and a spectrometer 220. Communication channels 216 provide communication between storage devices 202, communication unit(s) 204, receiver 206, processor(s) 208, one or more microphones 210, and sensors 212. Components 202, 204, 206, 208, 210, 212 and 220 may draw electrical power from power source 214.

In the example of FIG. 2, components 202, 204, 206, 208, 210, 212, 214, 216 and 220 are contained within a single housing 218. However, in other examples of this disclosure, components 202, 204, 206, 208, 210, 212, 214, 216 and 220 may be distributed among two or more housings. For instance, in an example where hearing instrument 102A is a RIC device, receiver 206 and one or more of sensors 212 may be included in an in-ear housing separate from a behind-the-ear housing containing the remaining components of hearing instrument 102A. In such examples, a RIC cable may connect the two housings.

Furthermore, in the example of FIG. 2, sensors 212 include an inertial measurement unit (IMU) 226 configured to generate data regarding the motion of hearing instrument 102A. IMU 226 may include a set of sensors. For instance, in the example of FIG. 2, IMU 226 includes one or more accelerometers 228, a gyroscope 230, a magnetometer 232, combinations thereof, and/or other sensors for determining the motion of hearing instrument 102A. Furthermore, in the example of FIG. 2, hearing instrument 102A may include one or more additional sensors 236, a photoplethysmography (PPG) sensor 238, body temperature sensors 240, environmental temperature sensors 242 and UV sensor 244. Additional sensors 236 may include blood oximetry sensors, blood pressure sensors, electrocardiograph (EKG) sensors, electroencephalography (EEG) sensors, environmental pressure sensors, environmental humidity sensors, skin galvanic response sensors, and/or other types of sensors. In other examples, hearing instrument 102A and sensors 212 may include more, fewer, or different components.

Storage device(s) 202 may store data. Storage device(s) 202 may comprise volatile memory and may therefore not retain stored contents if powered off. Examples of volatile memories may include random access memories (RAM), dynamic random access memories (DRAM), static random access memories (SRAM), and other forms of volatile memories known in the art. Storage device(s) 202 may further be configured for long-term storage of information as non-volatile memory space and retain information after power on/off cycles. Examples of non-volatile memory configurations may include flash memories, or forms of electrically programmable memories (EPROM) or electrically erasable and programmable (EEPROM) memories.

Communication unit(s) 204 may enable hearing instrument 102A to send data to and receive data from one or more other devices, such as a device of computing system 108 (FIG. 1), another hearing instrument (e.g., hearing instrument 102B), an accessory device, a mobile device, or another types of device. Communication unit(s) 204 may enable hearing instrument 102A to use wireless or non-wireless communication technologies. For instance, communication unit(s) 204 enable hearing instrument 102A to communicate using one or more of various types of wireless technology, such as a BLUETOOTH™ technology, 3G, 4G, 4G LTE, 5G, ZigBee, WI-FI™, Near-Field Magnetic Induction (NFMI), ultrasonic communication, infrared (IR) communication, or another wireless communication technology. In some examples, communication unit(s) 204 may enable hearing instrument 102A to communicate using a cable-based technology, such as a Universal Serial Bus (USB) technology.

Receiver 206 comprises one or more speakers for generating audible sound. Microphone(s) 210 detect incoming sound and generate one or more electrical signals (e.g., an analog or digital electrical signal) representing the incoming sound.

Processor(s) 208 may be processing circuits configured to perform various activities. For example, processor(s) 208 may process signals generated by microphone(s) 210 to enhance, amplify, or cancel-out particular channels within the incoming sound. Processor(s) 208 may then cause receiver 206 to generate sound based on the processed signals. In some examples, processor(s) 208 include one or more digital signal processors (DSPs). In some examples, processor(s) 208 may cause communication unit(s) 204 to transmit one or more of various types of data. For example, processor(s) 208 may cause communication unit(s) 204 to transmit data to computing system 108. In some examples, processor(s) 208 may read instructions from storage device(s) 202 and may execute instructions stored by storage device(s) 202. Execution of the instructions by processor(s) 208 may configure or cause hearing instrument 102A to provide at least some of the functionality ascribed in this disclosure to computing device 300. Furthermore, communication unit(s) 204 may receive audio data from computing system 108 and processor(s) 208 may cause receiver 206 to output sound based on the audio data.

Spectrometer 220 may be an ultra-compact spectrometer chip such as a Hamamatsu C12666MA manufactured by Hamamatsu Photonics of Shizuoka, Japan. The spectrometer 220 may be built within a chip and may be integrated into the housing 218 of the hearing instrument 102A. Spectrometer 220 may have the ability to distinguish energy received at several spectral ranges and determine the amount of UV and any other color of light received. Spectrometer 220 may operate similarly to a light sensor. Spectrometer 220 may be used to detect UV, visible light and infrared light. The spectrum of light covered may be from 100 nm up to 1 mm. Spectrometer 220 may offer an alternative to UV sensor 244 and/or PPG sensor 238 and/or spectrometer 220 may improve upon the data already provided by UV sensor 244 and PPG sensor 238.

Spectrometer 220 may be an optical spectrometer (often simply called a "spectrometer") that indicates the intensity of light as a function of wavelength or of frequency. Deflection is produced either by refraction in a prism or by diffraction in a diffraction grating. Spectrometers utilize the phenomenon of optical dispersion. The light from a source may consist of a continuous spectrum, an emission spectrum (bright lines), or an absorption spectrum (dark lines). Because each element leaves its spectral signature in the pattern of lines observed, a spectral analysis may reveal the composition of the object analyzed.

According to various examples, the power source 214 includes an energy storing device contained in housing 218. Examples of energy storing devices include, but are not limited to, batteries, capacitors, and inductors, and rechargeable batteries, capacitors, and inductors. The term battery, used for various examples, may be used for other types of energy storing devices for purposes of this disclosure.

In varying examples, the power source 215 includes charging circuitry 215. The charging circuitry 215 is adapted to charge power source 214 within the hearing instrument 102A. In another example, the power source 214 is separate from charging circuitry 215. Charging circuitry 215 may receive energy from other devices, such as UV sensor 244, discussed in greater detail below, and charge power source 214. In another example, charging circuitry 215 in configured to couple directly to UV sensor 244 and power source 214 to convert energy sent by UV sensor 244 into a charging energy conditioned to charge power source 214.

Figure 3:
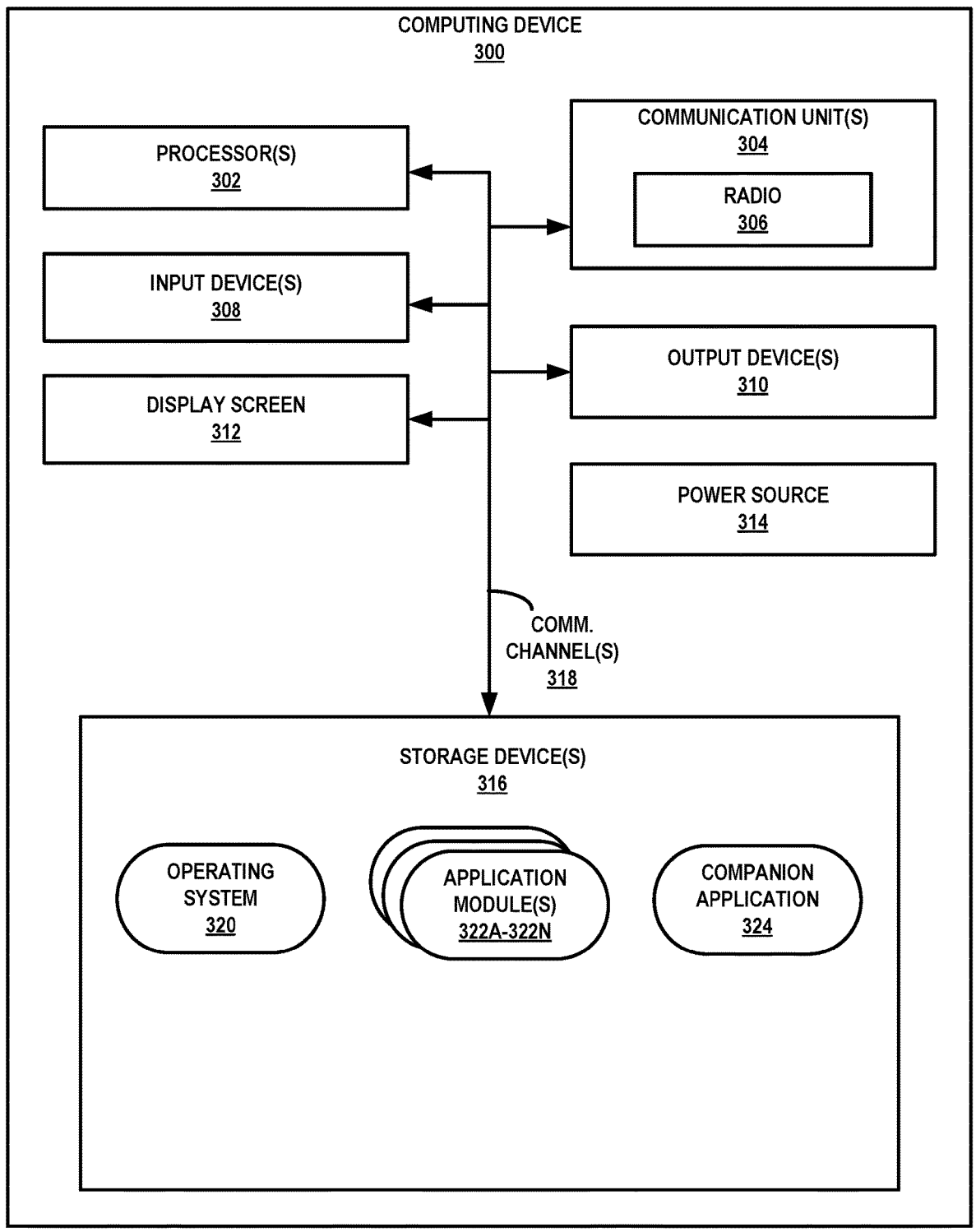
FIG. 3 is a block diagram illustrating example components of a computing device, in accordance with one or more techniques of this disclosure.

FIG. 3 is a block diagram illustrating example components of computing device 300, in accordance with one or more techniques of this disclosure. FIG. 3 illustrates only one particular example of computing device 300, and many other example configurations of computing device 300 exist. Computing device 300 may be a computing device in computing system 108 (FIG. 1).

As shown in the example of FIG. 3, computing device 300 includes one or more processors 302, one or more communication units 304, one or more input devices 308, one or more output devices 310, a display screen 312, a power source 314, one or more storage devices 316, and one or more communication channels 318. Computing device 300 may include other components. For example, computing device 300 may include physical buttons, microphones, speakers, communication ports, and so on. Communication channel(s) 318 may interconnect each of components 302, 304, 308, 310, 312, and 316 for inter-component communications (physically, communicatively, and/or operatively). In some examples, communication channel(s) 318 may include a system bus, a network connection, an inter-process communication data structure, or any other method for communicating data. Power source 314 may provide electrical energy to components 302, 304, 308, 310, 312 and 316.

Storage device(s) 316 may store information required for use during operation of computing device 300. In some examples, storage device(s) 316 have the primary purpose of being a short term and not a long-term computer-readable storage medium. Storage device(s) 316 may be volatile memory and may therefore not retain stored contents if powered off. Storage device(s) 316 may further be configured for long-term storage of information as non-volatile memory space and retain information after power on/off cycles. In some examples, processor(s) 302 on computing device 300 read and may execute instructions stored by storage device(s) 316.

Computing device 300 may include one or more input device(s) 308 computing device 300 uses to receive user input. Examples of user input include tactile, audio, and video user input. Input device(s) 308 may include presence-sensitive screens, touch-sensitive screens, mice, keyboards, voice responsive systems, microphones or other types of devices for detecting input from a human or machine.

Communication unit(s) 304 may enable computing device 300 to send data to and receive data from one or more other computing devices (e.g., via a communications network, such as a local area network or the Internet). For instance, communication unit(s) 304 may be configured to receive data exported by hearing instrument(s) 102, receive data generated by user 104 of hearing instrument(s) 102, receive and send request data, receive and send messages, and so on. In some examples, communication unit(s) 304 may include wireless transmitters and receivers enabling computing device 300 to communicate wirelessly with the other computing devices. For instance, in the example of FIG. 3, communication unit(s) 304 include a radio 306 enabling computing device 300 to communicate wirelessly with other computing devices, such as hearing instruments 102 (FIG. 1). Examples of communication unit(s) 304 may include network interface cards, Ethernet cards, optical transceivers, radio frequency transceivers, or other types of devices able to send and receive information. Other examples of such communication units may include BLUETOOTH™, 3G, 4G, 5G, and WI-FI™ radios, Universal Serial Bus (USB) interfaces, etc. Computing device 300 may use communication unit(s) 304 to communicate with one or more hearing instruments (e.g., hearing instrument 102 (FIG. 1, FIG. 2)). Additionally, computing device 300 may use communication unit(s) 304 to communicate with one or more other remote devices.

Output device(s) 310 may generate output. Examples of output include tactile, audio, and video output. Output device(s) 310 may include presence-sensitive screens, sound cards, video graphics adapter cards, speakers, liquid crystal displays (LCD), or other types of devices for generating output.

Processor(s) 302 may read instructions from storage device(s) 316 and may execute instructions stored by storage device(s) 316. Execution of the instructions by processor(s) 302 may configure or cause computing device 300 to provide at least some of the functionality ascribed in this disclosure to computing device 300. As shown in the example of FIG. 3, storage device(s) 316 include computer-readable instructions associated with operating system 320, application modules 322A-322N (collectively, "application modules 322"), and a companion application 324.

Execution of instructions associated with operating system 320 may cause computing device 300 to perform various functions to manage hardware resources of computing device 300 and to provide various common services for other computer programs. Execution of instructions associated with application modules 322 may cause computing device 300 to provide one or more of various applications (e.g., "apps," operating system applications, etc.). Application modules 322 may provide particular applications, such as text messaging (e.g., SMS) applications, instant messaging applications, email applications, social media applications, text composition applications, and so on.

Execution of instructions associated with companion application 324 by processor(s) 302 may cause computing device 300 to perform one or more of various functions. For example, execution of instructions associated with companion application 324 may cause computing device 300 to configure communication unit(s) 304 to receive data from hearing instruments 102 and use the received data to present data to a user, such as user 104 or a third-party user. In some examples, companion application 324 is an instance of a web application or server application. In some examples, such as examples where computing device 300 is a mobile device or other type of computing device, companion application 324 may be a native application.

Computing device 300 may provide information about a user's environment, which may be used by hearing instrument 102 in determining a user's environment; such as user 104 being indoors or outdoors. Computing device 300 may read local UVI (ultraviolet index) and climate information and communicate this information to hearing instrument 102. Hearing instruments 102 may use this UV and climate information to determine whether user 104 is located indoor or outdoor based upon sensor readings.

Figure 4:
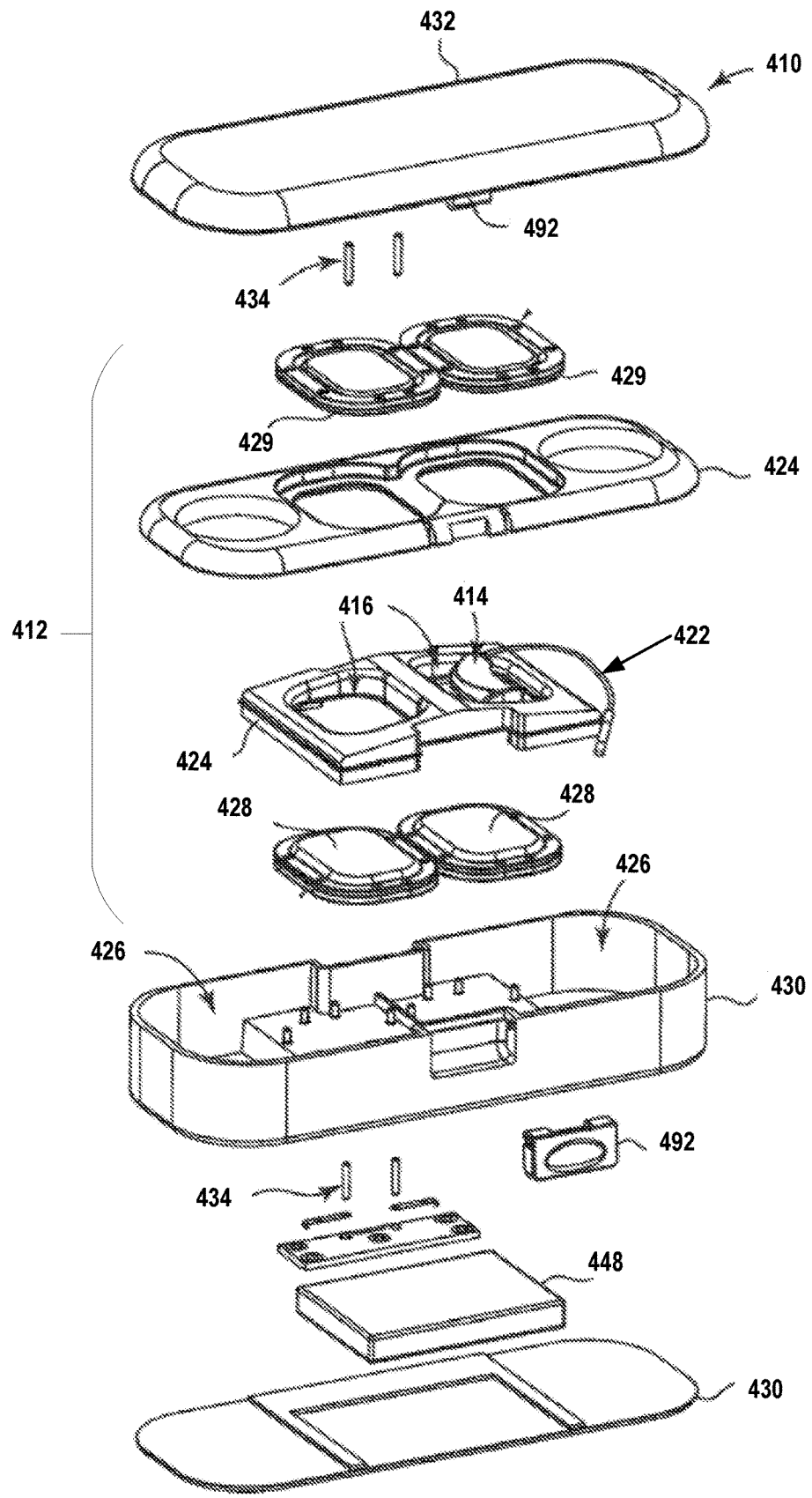
FIG. 4 is an overhead perspective view of a recharging system including an ultraviolet (UV) charging apparatus and a rechargeable device in accordance with one or more techniques of this disclosure.

FIG. 4 is an overhead perspective view of a recharging system including a UV charging apparatus and a rechargeable device in accordance with one or more techniques of this disclosure. An example recharging system 410 is shown including a UV charger 412 and a rechargeable hearing instrument 414. Rechargeable hearing instrument 414 may be a hearing instrument similar to 102A or 102B having a power source 214 and charging circuitry 215. As shown in the example of FIG. 4, rechargeable hearing instrument 414 is a BTE with a RIC. However, recharging system 410 may accept other types of hearing instruments. Rechargeable hearing instrument 414 may interface with UV charger 412 in a variety of orientations for charging and for protection while charging.

UV charger 412 has an open position in which UV charger 412 may receive rechargeable device 414 for charging. A charging cavity 416 may be defined by UV charger 412 for receiving a body of rechargeable device 414 (e.g., housing 218 (FIG. 2)) having a UV sensor 244 (see FIG. 2). An extension portion 422 of the rechargeable device 414 is receivable into a well 426 of the UV charger 412. Extension portion 422 may include a RIC cable and an in-ear receiver assembly. UV charger 412 may include a liner 424 and UV light sources 428, 429 that define charging cavity 416. UV light sources 428, 429 make it possible to charge the rechargeable hearing instrument 414. By having a dual-purpose UV sensor 244 and charge circuit in rechargeable hearing instrument 414, any charging contacts may be removed from the rechargeable hearing instrument 414 and from the UV charger 412. Charging contacts may be problematic because charging contacts may need to be protected from electrostatic discharge, increase material ingress probability and they may become corroded, thus lowering the charging efficiency.

Charging cavity 416 may be sized and shaped to receive any rechargeable hearing instrument 414 for charging. For example, rechargeable hearing instrument 414 may be rested on either side and in various rotational orientations while resting in charging cavity 416.

UV charger 412 may include a base 430 and a lid 432, which may be opened for exposing charging cavity 416 and may be closed to initiate charging of rechargeable hearing instrument 414. UV charger 412 may also include a pin assembly 434 for disconnecting the electrical connection between UV light sources 428 of base 430 and UV light sources 429 of lid 432, for example, when lid 432 is opened. In some examples, rechargeable hearing instrument 414 may not be charged until lid 432 is closed.

Rechargeable hearing instrument 414 may be a hearing device, such as those discussed above and the BTE, as shown in the illustration. As discussed above, rechargeable hearing instrument 414 may have a UV sensor 244. UV sensor 244 may be placed within the housing 218. UV sensor 244 provides a charging path from the exterior (e.g., outer surface) of rechargeable hearing instrument 414 to a power source 214 (see FIG. 2) within housing 218, which may be used to power rechargeable hearing instrument 414 and may require recharging from time-to-time. Housing 218 may include more than one UV sensor 244.

In some examples, rechargeable hearing instrument 414 may be placed in UV charger 412 in any manner. For example, UV light source 429 of lid 432 provides enough UV light to charge rechargeable hearing instrument 414 if rechargeable hearing instrument 414 is placed within cavity 416 where UV sensor 244 is only facing lid 432. Similarly, if rechargeable hearing instrument 414 is turned where UV sensor 244 is facing base 430, UV light source 428 provides enough light to charge rechargeable hearing instrument 414. Further, when UV light sources 428 and 429 are radiating UV light, the UV light may radiate throughout cavity 416. In some examples, cavity 416 is covered in a reflective coating where the UV light may fill the entire cavity thus providing UV sensor 244 with enough UV light to create a voltage capable of providing a charge to power source 214. In some examples, one or both of the UV charger 412 and the rechargeable hearing instrument 414 may include power management electronics.

Lid 432 may be moved into a closed position with rechargeable hearing instrument 414 in place, and lid 432 may be secured to base 430 by a securing mechanism 492, such as a releasable tab and detent assembly. In the closed position, UV light sources 428, 429 may power on or the user may select an on/off switch so lid 432 may be closed to prevent dust from accumulating in cavity 416 without powering on UV light sources 428, 429.

Pin assembly 434 of UV charger 412 may be at least partially disposed on base 430 and lid 432. For example, pin assembly 434 may include two opposing pins (e.g., pogo pins), with one attached to each of base 430 and lid 432, and at least one pin being spring-loaded to engage the other when lid 432 is closed. Pin assembly 434 may separate the pins to electrically uncouple or disconnect one or more UV sources 429 of lid 432 from power source 448 when lid 432 is opened. The separable portions of pin assembly 434 may engage to electrically couple or connect UV sources 429 of lid 432 to power source 448 when lid 432 is closed. As the opposing pins engage and disengage, the pins may scratch one another, thereby removing debris from one another.

In some examples, UV charger 412 includes a power switch (e.g., an on/off switch). In some examples, closing lid 432 turns on UV charger 412 or otherwise completes a circuit to activate charging and opening lid 432 turns off UV charger 412 or otherwise breaks the circuit. With the addition of UV sensor 244, hearing instrument 102, 414 may user the UV converted energy to charge power source 214. High power UV LEDs 428 and 429 provide the UV light source for UV sensor 244. With a dual-purpose UV sensor 244 and charge circuit, charging contacts may be removed from hearing instrument 102.

Figure 5:
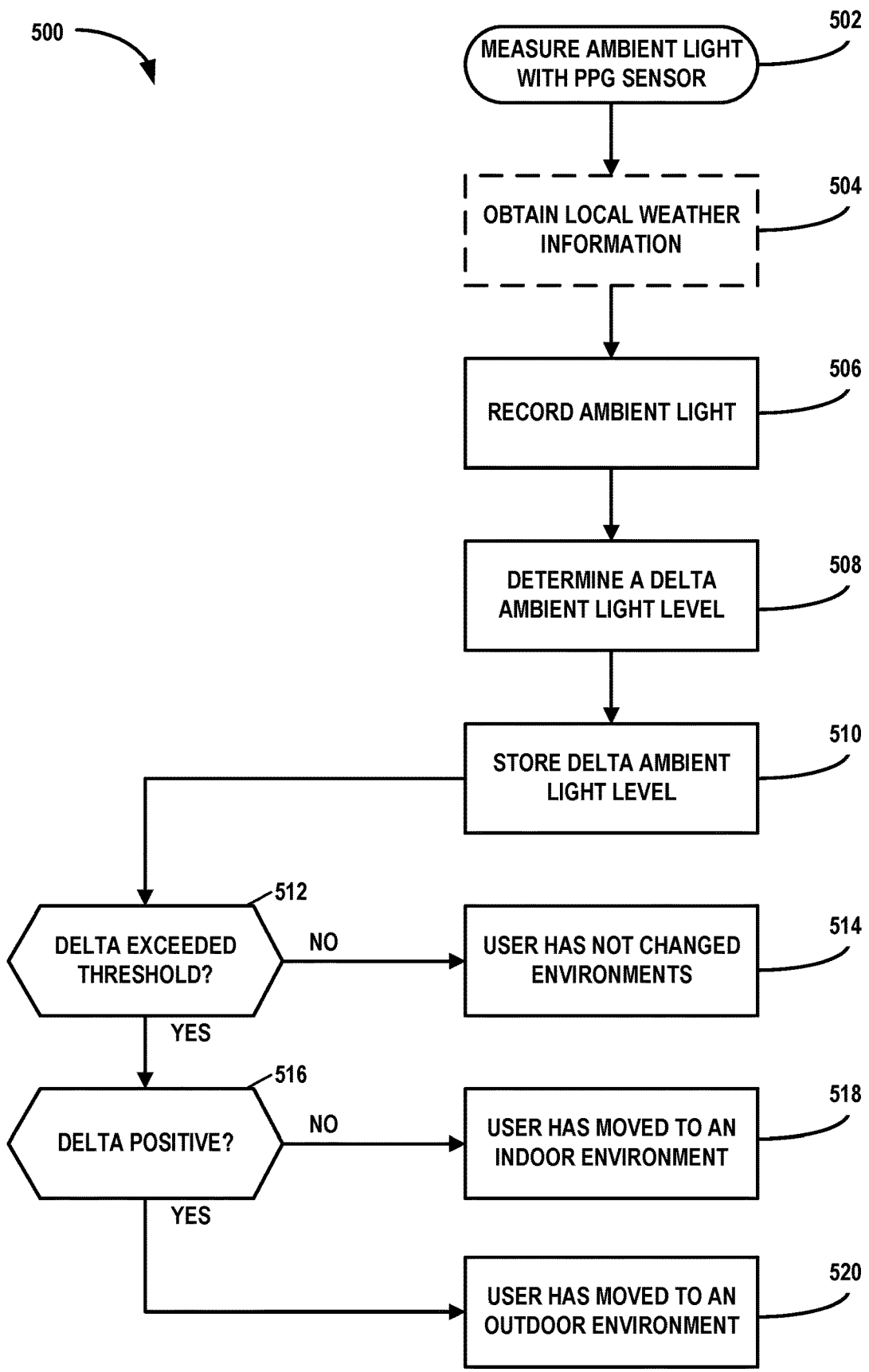
FIG. 5 is a flowchart illustrating an example operation in which processors of a hearing instrument categorize an environment of a user based on signals from a photoplethysmography (PPG) sensor, in accordance with one or more techniques of this disclosure.

FIG. 5 is a flowchart illustrating an example operation 500 in which processor(s) 208 of hearing instrument 102A categorizes an environment of user 104 based on signals from PPG sensor 238, in accordance with one or more techniques of this disclosure. Other examples of this disclosure may include more, fewer, or different actions, or actions may be performed in different orders. Although the example of FIG. 5 is described with respect to hearing instrument 102A, FIG. 5 may be equally applicable to hearing instrument 102B.

PPG sensor 238 may comprise an onboard light-emitting diode (LED) and a set of one or more photodiodes. The onboard LED of PPG sensor 238 outputs flashes of light. The photodiodes of PPG sensor 238 generate electrical signals in response to light, include the flashes of light generated by the onboard LED of PPG sensor 238. The electrical signals generated by the photodiodes of PPG sensor 238 may be dependent on the amount of light transmitted or reflected to the photodiodes of PPG sensor 238. In other words, the electrical signals generated by the photodiodes of PPG sensor 238 may be dependent on the level of light striking the photodiodes of PPG sensor 238. Human skin absorbs and reflects different amount of light depending on blood perfusion within the skin. The blood perfusion is modulated with heart rate. Hence, by monitoring the electrical signals generated by the photodiodes of PPG sensor 238 in response to flashes of light generated by the onboard LED of PPG sensor 238, processor(s) 208 may determine the heart rate of user 104.

In general, it is only necessary for the photodiodes of PPG sensor 238 to measure overall light levels, and not light levels at particular wavelengths, to determine the heart rate of user 104. Hence, PPG sensor 238 may not be configured to distinguish the wavelengths of light detected. Rather, photons striking the photodiodes of PPG sensor 238 may be converted to electrical signals from which the original wavelengths (or energy level) may not be distinguished.

In accordance with a technique of this disclosure, hearing instrument 102A may use ambient light levels detected by PPG sensor 238 to categorize a current environment of user 104. The ambient light level is a light level in between flashes of the onboard LED of PPG sensor 238. Using ambient light levels detected by PPG sensor 238 to categorize the current environment of user 104 may be advantageous because PPG sensor 238 may potentially be used for both categorizing the current environment of user 104 and also detecting the heart rate of user 104.

However, there may be a number of challenges associated with using PPG sensor 238 to categorize the current environment of user 104 and detect the heart rate of user 104. For example, PPG sensor 238 may face the skin of user 104 to measure the heart rate of user 104. This may cause problems in detecting ambient light levels because the ambient light levels detected by PPG sensor 238 may depend on skin pigmentation of user 104, a level of fit of hearing instrument 102A, internal structures and composition of tissue in contact with PPG sensor 238, and/or other factors. These variables make it difficult to set a universal threshold for all users in determining the current environment of the users, such as whether the users are indoors or outdoors. Similarly, going outdoors on a cloud day versus a sunny day may also increase the difficulty of determining the current environment of user 104.

The techniques of this disclosure may address one or more of these challenges. For instance, in the example of FIG. 5, operation 500 may begin with PPG sensor 238 measuring an ambient light level at the hearing instrument 102A to provide a measurement result (502). The ambient light level is a light level in between flashes of the onboard LED of PPG sensor 238. In accordance with a technique of this disclosure, hearing instrument 102A may use the detected ambient light level to categorize a current environment of user 104.

Furthermore, in the example of FIG. 5, processor(s) 208 of hearing instrument 102A may obtain local weather information (504). The local weather information may include information about the weather (e.g., current temperature, current cloudiness, current relative humidity, etc.) of a location of user 104. The local weather information may indicate whether the current weather is cloudy or rainy. In such a weather condition, the ambient light level threshold to indicate an "outdoor" condition may be set lower than when the weather is sunny. In addition to the UV thresholds the IR/UV ratios (discussed in more detail below) can be adjusted as well with weather information. Processor(s) 208 may obtain the local weather information in one or more of a variety of ways. For example, processor(s) 208 may obtain the local weather information via a wireless or wired-based communication link with computing system 108 (FIG. 1) or another computing system. In some examples, processor(s) 208 may communicate with a mobile telephone of user 104 to retrieve the local weather information from a remote server. In some examples, processor(s) 208 may categorize the current environment of user 104 without obtaining the local weather information. Hence, the action of processor(s) 208 obtaining the local weather information is indicated in a broken line.

In the example of FIG. 5, storage device 202 of hearing instrument 202 may record or store data indicating the ambient light level detected by PPG sensor 238 (506). Further, processor(s) 208 may determine a delta ambient light level based on the ambient light level detected by PPG sensor 238 (508). The delta ambient light level indicates a difference between the ambient light level detected by PPG sensor 238 and a previous ambient light level detected by PPG sensor 238. For example, the delta ambient light level may indicate a change between an ambient light level detected by PPG sensor 238 at time $t_i$ and a previous ambient light level detected by PPG sensor 238 at time $t_{i-1}$. Storage device 202 may also store or record the delta ambient light levels (510).

Processor(s) 208 may determine the current environment of user 104 based on the delta ambient light level. For instance, in the example of FIG. 5, processor(s) 208 may determine if an absolute value of the delta ambient light level exceeds a predetermined threshold (512). Processor(s) 208 may perform this determination on a periodic basis, on an event-driven basis, or according to another regime.

If the absolute value of the delta ambient light level does not exceed the threshold ("NO" branch of 512), then processor(s) 208 may determine that the current environment of user 104 has not changed (514). For purposes of examples of the disclosure, threshold may be defined as the magnitude or intensity that must be exceeded for a certain reaction, phenomenon, result, or condition to occur or be manifested. The threshold may be a predetermined number based upon the user's location (e.g., a user located near the equator vs. a user located in the northern hemisphere). The threshold may be a reading twice, three times, four times or more of a normal indoor ambient light level. The threshold cold be definable based upon the user's habits. Thus, hearing instrument 102 may ask user 104 if he/she is outside when the ambient light level nears or exceeds the threshold. If user 104 answers affirmatively, hearing instrument 102 may set the measured delta value as a new threshold for further operation.

However, in response to determining that the absolute value of the delta ambient light level exceeds the threshold ("YES" branch of 512), processor(s) 208 may determine if the delta ambient light level is positive (516). If the delta ambient light level is threshold is not positive (i.e., the delta ambient light level is negative) ("NO" branch of 516), processor(s) 208 may determine that user 104 has moved to an indoor environment from an outdoor environment (518). If the delta ambient light level is positive ("YES" branch of 516), processor(s) 208 may determine that user 104 has moved to an outdoor environment from an indoor environment (520).

Using changes in ambient light level (i.e., delta ambient light levels) over a predetermined time period, such as a typical day, and not absolute levels of ambient light may resolve one or more of the challenges described above with respect to using PPG sensor 238 to determine the current environment of user 104. Typically, the delta (i.e., change) of ambient light levels from indoor to outdoor is a magnitude larger than most changes in a typical indoor environment, even on a cloudy day. Thus, with certain exceptions (e.g., the user 104 purposely exposing themselves to a sunlamp for an extended period of time), processor(s) 208 may be able to distinguish the relative change from indoor to outdoor, even if the current environment of user 104 may not be determined based solely on absolute ambient light levels detected by PPG sensor 238.

In some examples, PPG sensor 238 may be modified to assist in the environment operation 500. Optical materials may be used to filter the wavelengths of light detected by PPG sensor 238 so that PPG sensor 238 is at least only sensitive to a certain frequency range of light. This filtering may better differentiate between a bright indoor environment, which has high levels of visible photons and thus not be confused with the outdoors which also has high levels of IR light. For example, an optical coating may be applied to PPG sensor 238 which would only allow a handful of specific wavelengths to enter the sensor, but still block out most other wavelengths. Through filtering, PPG sensor 238 may reduce any light frequencies that PPG sensor 238 is unconcerned with or which may cause a false reading at PPG sensor 238. By filtering out the wavelengths by IR light, the absolute delta ambient light levels between indoor and outdoor light will be larger. Further, flipping a light switch to the on position indoors may change the ambient light levels in the visible range, but not change the ambient light levels in the IR range. Thus, while the ambient light levels may indicate a change from inside to outside the IR range would not provide such an indication. The filter/coating may also allow through the frequency of the light generated by the LED of PPG sensor 238. Thus, PPG sensor 238 may also be used for regular PPG heart rate detection.

In some examples, multiple photosensors, which are sensitive to a specific wavelength for each photosensor, may be used. Thus, an optical coating on PPG sensor 238 may not be necessary as hearing instrument 102 would have a photosensor for each wavelength of interest (e.g., ambient, IR) and filtering of PPG sensor 238 may not be necessary as the photosensors would provide accurate data. Further, an optical grating or hologram may be used to separate the multiple wavelengths and then sensed on multiple photodetectors. The optical grating or hologram may split the wavelengths and route to multiple photodetectors or PPG sensor 238 thus ensuring only wavelengths of interest are measured. An optical grating or hologram may employ a similar technique as described above in relation to spectrometer 220. Using a grating or prism the light is spread into different wavelengths and multiple sensors may be used to sense a wavelength of interest. The grating separates the light into different frequencies (e.g., like a rainbow) and then only specific frequencies land on specific sensors.

UV sensor 244 may be integrated into the determination of whether user 104 is indoors or outdoors. UV sensor 244 may measure the amount of UV light received, which allows the same type of environment categorization at discussed with reference to FIG. 5. However, UV sensor 244 may offer improved indoor/outdoor resolution. A UV measurement may also allow processor(s) 208 to determine an amount of UV exposure user 104 has had and provide notifications to user 104 in the event of overexpose to UV radiation. Further, a detection of a UV measurement higher than a reference threshold, by processor(s) 208, may be considered exposure to an artificial UV light source (e.g., a UV disinfection lamp in a hospital). Additionally, computing device 300 may provide local UVI (ultraviolet index) and climate information which may be used as a reference to provide a better determination of whether user 104 was indoor or outdoor. If the UVI is low on certain day, the threshold may be set lower and vice versa if the UVI is higher on a certain day. It may assist in making an outdoor classification more accurate.

Figure 6:
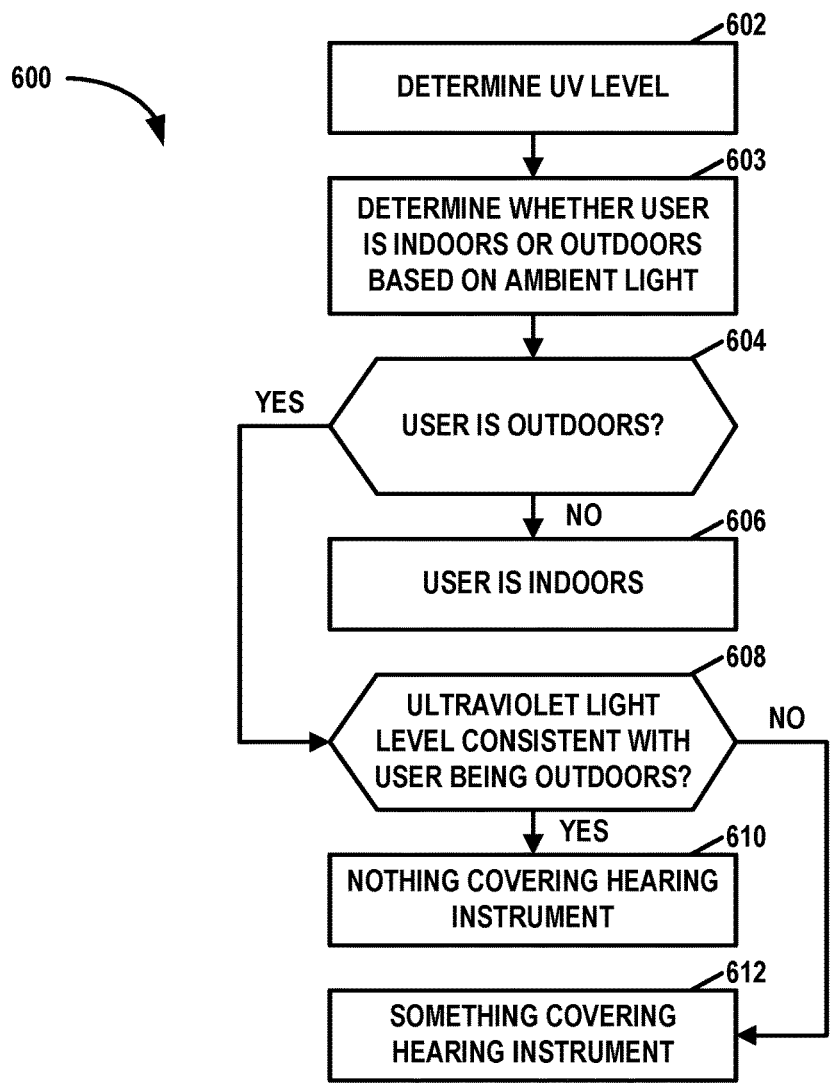
FIG. 6 is a flowchart illustrating an example operation to determine whether a hearing instrument is covered in accordance with one or more techniques described in this disclosure.

FIG. 6 is a flowchart illustrating an example operation 600 to determine whether hearing instrument 102A is covered in accordance with one or more techniques described in this disclosure. Although FIG. 6 is described with respect to hearing instrument 102A and components thereof, the discussion of FIG. 6 may apply equally with respect to hearing instrument 102B and components of hearing instrument 102B.

In the example of FIG. 6, processor(s) 208 may determine a UV light level (602). The UV light level may be a level of UV light detected by a sensor (e.g., UV sensor 244, spectrometer 220, etc.) of hearing instrument 102A. Processor(s) 208 may determine whether user 104 is indoors or outdoors based on ambient light, e.g., ambient light detected by PPG sensor 238 (603). Processor(s) 208 may determine whether user 104 is indoors or outdoors based on ambient light detected by PPG sensor 238 in one of a variety of ways. For example, processor(s) 208 may perform the method of FIG. 5 to determine whether user 104 is indoors or outdoors based on ambient light detected by PPG sensor 238. In some examples, processor(s) 208 may use a signal generated by spectrometer 220 to determine whether user 104 is indoors or outdoors.

Further, processor(s) 208 may also use an input from a spectrometer 220 to assist in determining whether user 104 is indoors or outdoors. Processor(s) 208 may then make a better determination whether user 104 was indoors or outdoors. For example, processor(s) 208 may base the determination on whether a weighted average; such as two or more inputs (e.g., a UV level and an ambient light level) indicate the user 104 is indoors; therefore, the user 104 is determined to be indoors. In another example, each input may be weighted based upon its reliability. Spectrometer 220 may be weighted more heavily because spectrometer 220 is able to differentiate between the wavelengths, UV sensor 244 may be weighted lower and PPG sensor 238 may be weighted even lower because PPG sensor 238 may be unable to differentiate between the wavelengths. Then, based upon the weighted averages, processor(s) 208 may determine if a set threshold based upon the weighted averages are surpassed to determine whether user 104 is indoors or outdoors. For example, if spectrometer 220 had a 75% reliability rate in accurately predicting whether a user was indoors or outdoors, UV sensor 244 has a 65% reliability rate and PPG sensor 238 had a 50% reliability rate; then a possible weighted value may be represented by the equation: weighted value=[0.75*spectrometer value+0.65*UV value+ 0.5*PPG value].

If the user is not outdoors (e.g., if threshold is not met or surpassed) ("NO" branch of 604), processor(s) 208 determines user 104 is indoors (606). If the user is outdoors (e.g., the threshold is met or surpassed) ("YES" branch of 604), processor(s) 208 may determine whether a UV light level is consistent with user 104 being outdoors (608). If the UV light level is consistent with user 104 being outdoors ("YES" branch of 608), processor(s) 208 may determine nothing is covering hearing instrument 102A (610). If the UV light level is not consistent with user 104 being outdoors ("NO" branch of 608), processor(s) 208 may determine something is covering hearing instrument 102A (612). For example, a user's hair, a user's hat, a user's coat or any other obstruction may be covering hearing instrument 102A. If any object is covering hearing instrument 102A, the obstruction may throw off calculations and determinations hearing instrument 102A performs for user 104; such as temperature calculations, which are discussed in greater detail below.

A determination of whether the UV light level is consistent with user 104 being outdoors can be made in a number of ways. For example, if spectrometer 220 senses an infrared (IR) input possibly detecting an outdoor environment (i.e., IR light is greater outdoor than indoors), but UV sensor 244 does not have an increased input, expected relative to an IR/UV ratio of outdoor light, then a determination may be made that something is covering hearing instrument 102A. The IR/UV ratio derives from the sun and atmosphere absorption spectrums. The ratio is very consistent across the Earth but may change with time of day because the sun has to travel through a larger amount of atmosphere at sun down versus sun up. For example, since UV light is absorbed more readily than IR light by hair, processor(s) 208 may determine whether hair is covering the hearing instrument 102A. Additionally, a reference UVI (i.e., the ultraviolet index or UV Index is an international standard measurement of the strength of UV radiation at a particular place and time) may be obtained for a given day from computing device 300. If a UV measurement made by UV sensor 244 is below the UVI, then processor(s) 208 may determine that something (e.g., the user's hair) is likely to be covering hearing instrument 102A. However, if other sensors onboard hearing instrument 102A are providing measurements consistent with user 104 being outdoors, then a determination may be made by processor(s) 208 user 104 has nothing covering hearing instrument 102A.

Figure 7:
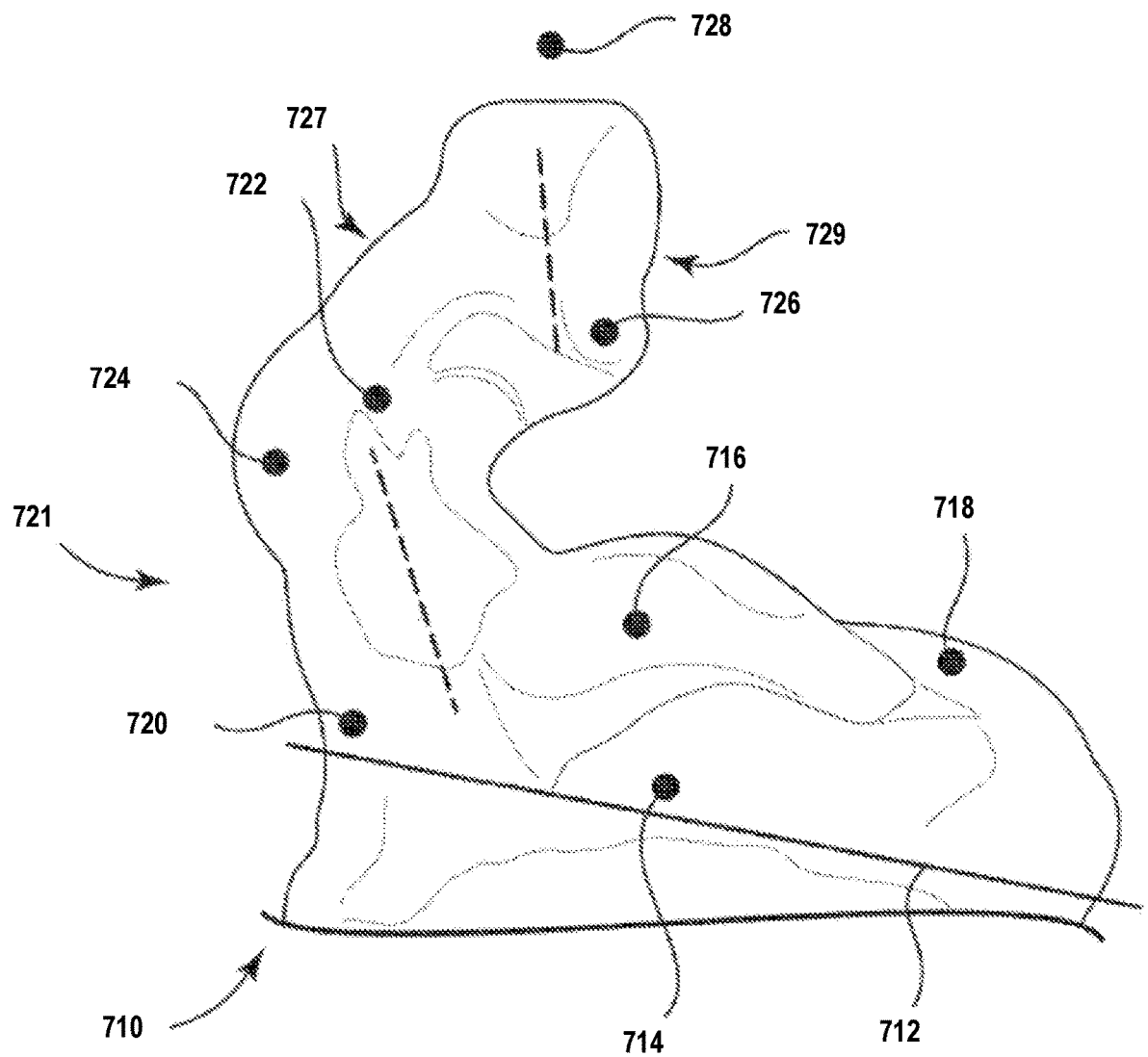
FIG. 7 is an illustration of a person's ear and, in particular, the ear canal.

FIG. 7 is an illustration of a person's ear 710 and, in particular, the ear canal 722. The ear 710 illustrated in FIG. 7 shows a number of anatomical features near the ear line 712, including the antitragus 714, concha 716, helix 718, and tragus 720. The ear canal 722 includes a proximal section 721 between the tragus 720 and a first bend 724 of the canal 722. A middle section 727 is shown between the first bend 724 and a second bend 726 of the canal 722. A distal section 729 is shown between the second bend 726 and an ear drum 728.

Figure 8:
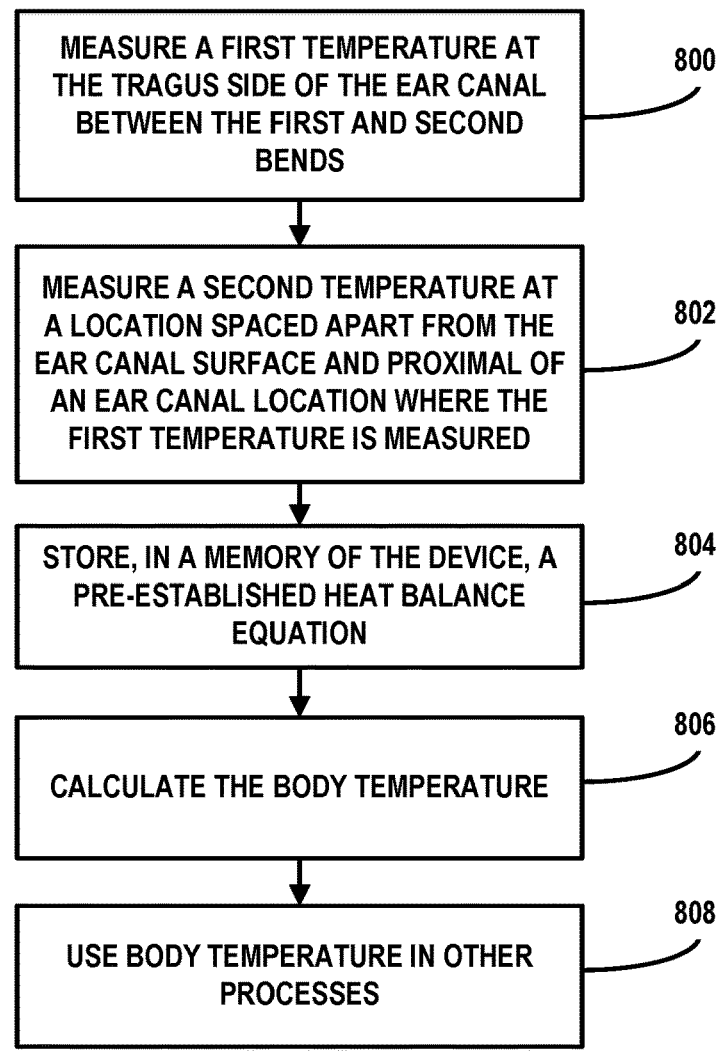
FIG. 8 is an example operation to determine a body temperature of a user in accordance with one or more techniques of this disclosure.

Hair detection or hearing instrument 102A obfuscation may be used for temperature compensation in which to provide a more accurate temperature reading in outdoor environments. The temperature in the ear may be slightly elevated when covered by hair as the hair acts an insulator and keeps the body warm. If it is known that hair is causing the ear canal to be slightly warmer (e.g., 0.5° C. warmer) a correction to the measurement may be made. FIG. 8 is an example operation to determine a body temperature of user 104 in accordance with one or more techniques of this disclosure. Examples are directed to devices and methods measuring temperature at a preferred location of ear canal 722 (FIG. 7), from which absolute core body temperature may be calculated using a heat balance equation in accordance with various examples. For example, two points in the ear canal could be measured. A difference between the two measurements could be multiplied by a factor and added to the inner temperature. Examples of FIG. 8 may be directed to devices and methods measuring temperature at a location of ear canal 722 (and other locations within or external of ear canal 722 as described herein) using a temperature sensor(s) configured to sense conductive (e.g., transferable through the skin) and/or convective heat (e.g., transferable through the air) rather than radiative heat.

In the example of FIG. 8 involves measuring 800 a first temperature with a first temperature sensor at the tragus-side 720 (FIG. 7) of the ear canal 722 between the first bend 724 and the second bend 726. Temperature sensors may be body temperature sensor 240, environmental temperature sensor 242 and/or part of additional sensors 236 on hearing instrument 102A. The method involves measuring a second temperature at a location spaced apart from a surface of the ear canal 722 and proximal of an ear canal location where the first temperature is measured (in an outer ear direction) (802). For example, the second temperature may be measured at a location spaced apart from the ear canal surface and exterior to the first bend 724 (e.g., within the ear canal or other outer ear location or exterior of the ear). By way of further example, the second temperature may be measured at a location spaced apart from the ear canal surface and exterior to the second bend 726 and interior to the first bend 724. The first and second temperatures are preferably indicative of conductive and/or convective heat, rather than radiative heat. The method further involves storing 804, in a storage device 202, a pre-established heat balance equation. Processor(s) 208 calculates the body temperature based on the first temperature, the second temperature, and data indicating whether hearing instrument 102A is covered (806). Processor(s) 208 may use the compensated body temperature for other processes of hearing instrument 102A (808). For example, if hair or other object were covering hearing instrument 102A, and the first and the second temperature sensor were providing a body temperature lower than actual as user 104 was outside in the sun, processor(s) 208 may correct for the difference in temperature measured due to the coverage of hearing instrument 102A by the user's hair, which would block the sun's rays causing an inaccurate temperature reading.

Figure 9:
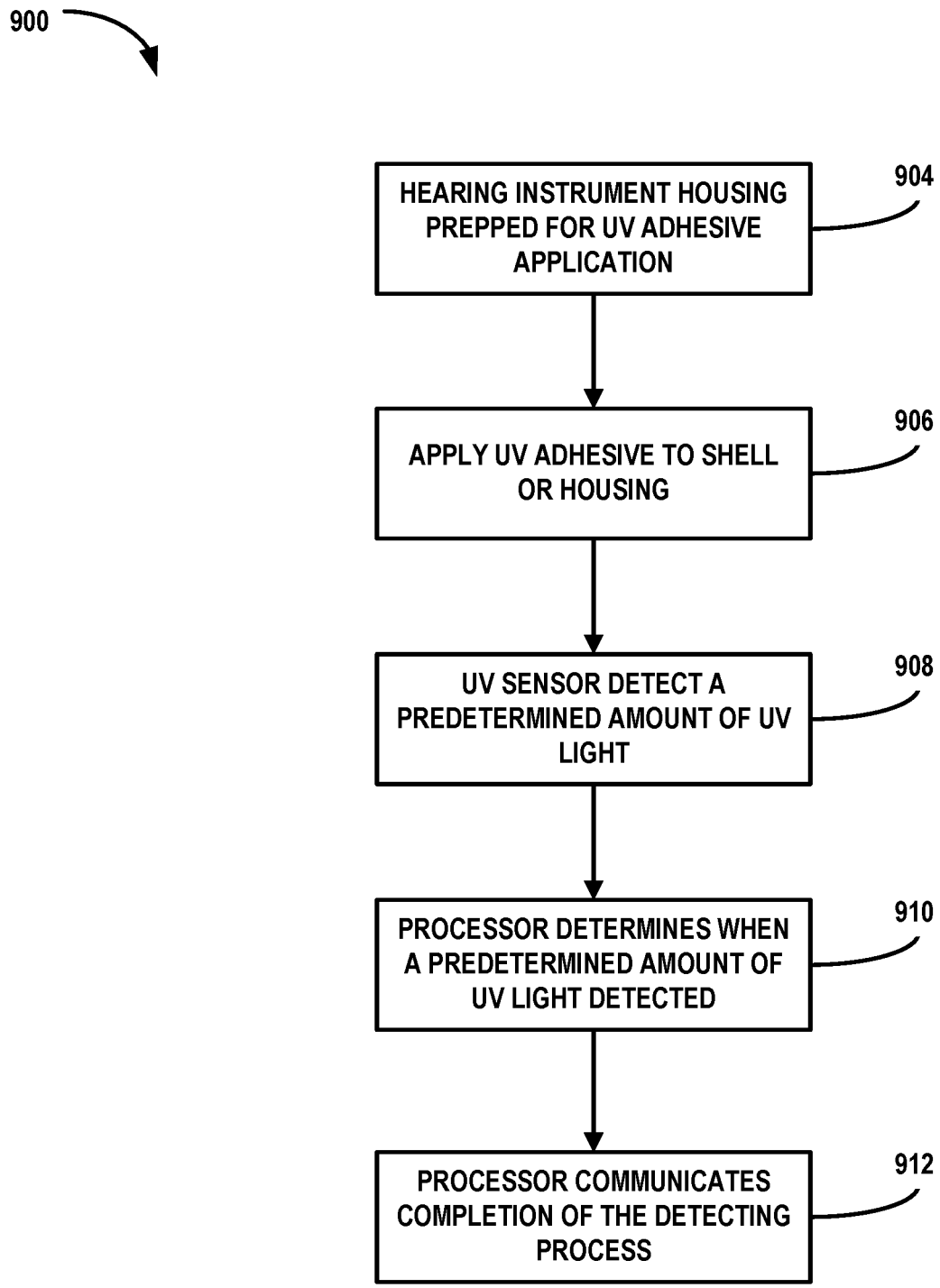
FIG. 9 is a flowchart illustrating an example operation in accordance with one or more techniques described in this disclosure.

FIG. 9 is a flowchart illustrating an example operation in accordance with one or more example techniques described in this disclosure. In a hearing instrument manufacturing process, it may be difficult to determine when a UV adhesive, used in the construction of the housing 218, is properly cured. As different UV lamps, used to cure the UV adhesive, may have different flux rates, the timing needed for curing the UV adhesive may vary and because of this efficiency in the manufacturing process may be lost based on the inability to know when a UV adhesive is properly cured.

In manufacturing operation 900, UV sensor 244 is utilized in a hearing instrument manufacturing process to measure the amount of time UV adhesive is exposed to UV light. A hearing instrument shell or housing 218 having internal electronics, like those identified in FIG. 2 are prepared to have a UV adhesive applied (904). A UV adhesive is applied to the shell or housing 218 which is cured utilizing UV light (906). UV sensor 244 may be utilized to sense the amount of UV light penetrating the shell or housing 218 (908). Processor(s) 208 may determine when a predetermined amount of light is detected based upon the amount of UV light penetrating the housing 218 (910). For example, processor(s) 208 may determine whether the UV adhesive is properly cured. Based upon the amount of UV light penetrating the housing 218, processor(s) 208 may determine whether the UV adhesive is cured and thus make the curing process more efficient and timelier as the UV sensor 244 and processor(s) 208 may determine precisely when the UV adhesive is properly cured. This is due to the properties of UV adhesive and the amount of UV light to which the UV adhesive has been exposed. When processor(s) 208 determine the predetermined amount of UV light has been detected, a notification may be sent via communication unit(s) 204 to terminate the UV light source, notify a technician, or instruct a machine to remove the hearing instrument to a location associated with a next stage of an assembly process (912).

In this disclosure, ordinal terms such as "first," "second," "third," and so on, are not necessarily indicators of positions within an order, but rather may be used to distinguish different instances of the same thing. Examples provided in this disclosure may be used together, separately, or in various combinations. Furthermore, with respect to examples involving personal data regarding a user, it may be required such personal data only be used with the permission of the user.

Depending on the example, it is to be recognized certain acts or events of any of the techniques described herein may be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium facilitating transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media accessible by one or more computers or one or more processing circuits to retrieve instructions, code and/or data structures for implementation of the techniques described in this disclosure. A computer program product may include a computer-readable medium.

By way of example, and not limitation, such computer-readable storage media may comprise RAM, ROM, EEPROM, CD-ROM or other optical disk storage, magnetic disk storage, or other magnetic storage devices, flash memory, cache memory, or any other medium able to be used to store desired program code in the form of instructions or data structures and may be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some respects, the functionality described herein may be provided within dedicated hardware and/or software modules. Also, the techniques may be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method for operating a hearing instrument, the method comprising the following steps:
   measuring, with one or more sensors of the hearing instrument, an ambient light level at the hearing instrument;
   determining a delta ambient light level that indicates a change in the detected ambient light level detected by the one or more sensors of the hearing instrument at different times;
   recording the delta ambient light level;
   determining whether an absolute value of the delta ambient light level exceeds a predetermined threshold;
   determining, based on the absolute value of the delta ambient light level exceeding the predetermined threshold and the delta ambient light level being positive, a user has moved to an outdoor environment; and
   setting a signal processing parameter of the hearing instrument as a function of the determination the user is in the outdoor environment or an indoor environment.

2. The method of claim 1, further comprising determining the user has not changed environments based on the predetermined threshold not being exceeded.

3. The method of claim 1, further comprising determining the user has moved to the indoor environment based on the delta ambient light level being negative.

4. The method of claim 1, wherein the sensor is a photoplethysmography (PPG) sensor.

5. The method of claim 4, wherein the PPG sensor has an optical coating to restrict detected wavelengths to wavelengths common to the indoor environment and the outdoor environment.

6. The method of claim 1, wherein the one or more sensors include multiple photosensors, each of the multiple photosensors being sensitive to a specific wavelength.

7. The method of claim 1, wherein the one or more sensors include an ultraviolet (UV) sensor.

8. The method of claim 1, wherein the one or more sensors include a spectrometer to determine a spectral range and intensity correlating to ambient light.

9. A hearing instrument comprising:
   one or more sensors configured to measure an ambient light level at the hearing instrument; and
   one or more processors configured to:
      determine a delta ambient light level that indicates a change in the detected ambient light level detected by the one or more sensors of the hearing instrument at different times;
      record the delta ambient light level;
      determine whether an absolute value of the delta ambient light level exceeds a predetermined threshold;
      determine, based on the absolute value of the delta ambient light level exceeding the predetermined threshold and the delta ambient light level being positive, a user has moved to an outdoor environment; and
      set a signal processing parameter of the hearing instrument as a function of the determination the user is in the outdoor environment or an indoor environment.

10. The hearing instrument of claim 9, wherein the one or more processors are further configured to determine the user has not changed environments based on the predetermined threshold not being exceeded.

11. The hearing instrument of claim 9, wherein the one or more processors are further configured to determine the user has moved to the indoor environment based on the delta ambient light level being negative.

12. The hearing instrument of claim 9, wherein the sensor is a photoplethysmography (PPG) sensor.

13. The hearing instrument of claim 12, wherein the PPG sensor has an optical coating to restrict detected wavelengths to wavelengths common to the indoor environment and the outdoor environment.

14. The hearing instrument of claim 9, wherein the one or more sensors include multiple photosensors, each of the multiple photosensors being sensitive to a specific wavelength.

15. The hearing instrument of claim 9, wherein the one or more sensors include an ultraviolet (UV) sensor.

16. The hearing instrument of claim 9, wherein the one or more sensors include a spectrometer to determine a spectral range and intensity correlating to ambient light.

* * * * *